United States Patent [19]
Cornelisse

[11] 4,372,925
[45] Feb. 8, 1983

[54] PROCESS FOR THE REMOVAL OF ACID GASES FROM GAS MIXTURES CONTAINING METHANE

[75] Inventor: Roelof Cornelisse, Calgary, Canada
[73] Assignee: Shell Oil Company, Houston, Tex.
[21] Appl. No.: 247,496
[22] Filed: Mar. 25, 1981

[30] Foreign Application Priority Data
Mar. 31, 1980 [NL] Netherlands ................ 8001886

[51] Int. Cl.³ .............................................. B01D 53/34
[52] U.S. Cl. .................................... 423/226; 423/228; 423/229; 423/573 R; 423/574 R; 55/73
[58] Field of Search ............ 423/226, 228, 224, 573, 423/573 R, 574 R; 55/68, 73

[56] References Cited
U.S. PATENT DOCUMENTS

| | | | |
|---|---|---|---|
| 3,120,993 | 2/1964 | Thormann et al. | 55/73 X |
| 3,161,461 | 12/1964 | Deal, Jr. et al. | 423/228 |
| 3,462,431 | 2/1972 | Suzuki et al. | 423/226 |
| 3,824,766 | 7/1974 | Valentine et al. | 55/73 X |
| 3,989,811 | 11/1976 | Hill | 423/228 X |
| 4,153,674 | 5/1979 | Verloop et al. | 423/574 R |
| 4,241,032 | 12/1980 | Werner et al. | 423/226 |
| 4,289,738 | 9/1981 | Pearce | 423/228 |

FOREIGN PATENT DOCUMENTS

| | | | |
|---|---|---|---|
| 1494800 | 7/1973 | Fed. Rep. of Germany | 423/228 |
| 1158976 | 7/1969 | United Kingdom | 423/226 |
| 1255201 | 1/1971 | United Kingdom | 423/228 |
| 1551692 | 8/1979 | United Kingdom | 423/228 |
| 2018281 | 10/1979 | United Kingdom | 423/226 |

*Primary Examiner*—Earl C. Thomas

[57] ABSTRACT

A process for the treatment of a gas mixture containing methane and light hydrocarbons is disclosed, the process being characterized in that the gas mixture is treated in two steps consecutively with two different liquid mixtures, each of which contains a physical and chemical absorbent, in the first step H₂S being selectively removed, in the second step the remaining acid gases being virtually completely removed.

13 Claims, 2 Drawing Figures

PROCESS FOR THE REMOVAL OF ACID GASES FROM GAS MIXTURES CONTAINING METHANE

BACKGROUND OF THE INVENTION

The invention relates to a process for the removal of acid gases from a gas mixture containing methane. Mixtures of this type occur mainly as natural gases; in addition to other hydrocarbons they generally contain acid gases such as hydrogen sulphide ($H_2S$) and carbon dioxide ($CO_2$). Natural gases usually also contain (in very small quantities) carbonyl sulphide (COS) and mercaptans.

Before natural gases can be condensed (for example for transport in the liquid state) or can be supplied as a gas to consumers via a pipe system, the acid gases, in particular $H_2S$, must be removed. Although some amount of $CO_2$ is acceptable if natural gases are to be transported in the gaseous state, the removal of the $CO_2$ down to a very low content is necessary if the gas is to be liquefied. Otherwise, deposition of solid $CO_2$ during the cooling of the gas can give rise to clogging. In general, substantial removal of COS and mercaptans is required in view of the requirements imposed in respect of the sulphur content of the final gas. The generally light hydrocarbons (such as propane, butanes and pentanes) which are present in the gas are also preferably separated from the gas because they represent a high value as liquid or compressed combustibles, and because if they form liquid deposits in pipe systems, they impede the transport of the gaseous methane.

In order to achieve the removal of these components from the natural gas as economically as possible, it is desirable to obtain the $H_2S$ in such a concentration that it can be processed to sulphur in a simple manner. This processing is generally carried out with advantage in a Claus process, in which $H_2S$ is converted into sulphur and water by reaction with $SO_2$. The most attractive manner of carrying out the Claus process is by supplying such a quantity of oxygen (for example, as air) to an $H_2S$-containing stream so that one third of the $H_2S$ is converted into $SO_2$ and the resultant quantity of $SO_2$ is consequently just sufficient to be converted with the remainder of the $H_2S$ into sulphur and water. This conversion can be carried out thermally and/or by means of a catalyst (for example, alumina). However, to carry out this process in the manner described, the quantity of $H_2S$ in the gas to be processed must be at least about 40% by volume. For economic reasons, of course, it is desirable that the $H_2S$ content of the gas to be processed is as high as possible. In the case of concentrations between 20 and 40% by volume, a Claus process is possible but special measures are necessary. In that case, one third of the $H_2S$ must be separated from the gas stream, this portion must be separately converted with air into $SO_2$, and this $SO_2$, together with the remaining $H_2S$, must be passed over a catalyst, thus forming sulphur and water. In the case of $H_2S$ concentrations below 20% by volume, even more complicated measures are necessary.

SUMMARY OF THE INVENTION

Accordingly, the invention provides a process in which a natural gas of such a high purity is obtained that it can be used both for condensation and for transport by pipeline, and an acid gas containing more than 40% by volume of $H_2S$ is also obtained. If the $H_2S$ percentage of the acid gases in the starting gas mixture is already 40% or more, the percentage can be further increased in the acid gas to be obtained by means of the process of the invention.

The invention, therefore, relates to a process for the removal of acid gases from a gas mixture mainly containing methane by treating said gas mixture with a liquid mixture which contains a physical and a chemical absorbent, characterized in that the gas mixture is treated at superatmospheric pressure in two steps consecutively with two different liquid mixtures which contain a physical absorbent and a chemical absorbent. In the first step, $H_2S$ is selectively removed with respect to $CO_2$, and in the second step, the remaining acid gases are virtually completely removed.

By a physical absorbent is meant a substance in which acid gases are soluble but with which they do not react. By a chemical absorbent is meant a substance with which acid gases can be chemically bound. By means of both types of absorbents, acid gases can be removed from a gas mixture; the absorption capacity of a physical absorbent is mainly determined by the pressure of the acid gases, and of a chemical absorbent by the structure of said absorbent.

As indicated, in the first step, $H_2S$ is selectively removed with respect to $CO_2$. That is to say, the molar ratio of $H_2S$ and $CO_2$ absorbed in the liquid mixture, which contains a physical and a chemical absorbent, used in this step (designated the first mixture) is higher than that in the starting mixture.

The selectivity of the first mixture for $H_2S$ depends on the composition of the mixture and on the contact time of the gas to be treated with said mixture.

It has been found that the selectivity for $H_2S$ is mainly determined by the type of chemical absorbent used. The chemical absorbent in said first mixture very suitably comprises, at least partly and preferably completely, one or more tertiary amines, particularly tertiary amines which contain at least one hydroxyalkyl group. Triethanol amine, diethyl ethanol amine, and methyl diethanol amine are very suitable.

As the physical absorbent, many substances can be used in the first mixture. For example, N-methyl pyrrolidone, dimethyl formamide, dimethyl ether of polyethylene glycol, and sulfolane are very suitable.

It is advantageous if the first mixture also contains water, since, consequently, the first mixture loaded with acid gases can be regenerated by steam-stripping, and the quantity of light hydrocarbons absorbed in the first mixture during the treatment of the gas to be purified is then limited to a minimum.

The first mixture very suitably contains 5–35% by weight of water, 15–50% by weight of physical absorbent and 10–60% by weight of chemical absorbent; mixtures of methyl diethanol amine, sulfolane and water are preferred.

The selectivity of the first mixture for $H_2S$ in respect to $CO_2$ is also determined by the contact time of said mixture with the gas to be purified; the selectivity is higher as the contact time is shorter. As a matter of fact, the contact time must be long enough for sufficient $H_2S$ to be absorbed. For this reason it is preferred, but not necessary, to use a limited number of contact trays (for example, less than 10) in the absorption column in which the gas to be purified is contacted with the first mixture.

The first mixture loaded with acid gases is suitably regenerated (if desired, after being expanded in order to remove absorbed nonacid components, such as low hydrocarbons, which can be returned to the first step after compression) by stream-stripping in a regeneration column. The regenerated first mixture is then recycled to the absorption column. The acid gas mixture liberated during regeneration has such a high $H_2S$ content that it can be processed into sulphur without difficulty in a Claus process.

The gas liberated after treatment in the first step still contains considerable quantities of $CO_2$, a small quantity of $H_2S$, and if originally present, COS and mercaptans. These gases are treated in the second step, according to the invention, with a liquid mixture which contains a physical absorbent and a chemical absorbent (designated below the second mixture), which mixture is different from the first mixture. The composition of the second mixture is so chosen that said acid gases, and preferably also the other sulphur-containing compounds, are removed in such a degree that the resultant purified gas (if desired, after removal of lower hydrocarbons and water present therein) fulfills the requirements made for its liquefaction or its transport in the gaseous state.

The chemical absorbent in the second mixture very suitably comprises at least partly, and preferably completely, one or more primary and/or secondary amines. Primary and secondary amines which contain at least one hydroxyalkyl group are preferred. Examples are ethanol amine, diethanol amine and, in particular, di-isopropanol amine.

As the physical absorbent the same substances are suitable as in the first mixture; sulfolane is also preferred in the second mixture. The presence of water is also of advantage in the second mixture for the reasons mentioned in the description of the first mixture.

The second mixture very suitably contains 5–35% by weight of water, 15–50% by weight of physical absorbent and 10–60% by weight of chemical absorbent; the mixtures of di-isopropanol amine, sulfolane and water are preferred.

In the second step, longer contact times are preferably maintained between the second mixture and the gas to be purified than in the first step, in order to remove the acid gases as completely as possible. Therefore, use is generally made of an absorption column having more trays than in the first step and, further, the flow rate of the gas through the column can be lower.

The second mixture, loaded with acid gases, is suitably regenerated with steam in a regeneration column (if desired, after expansion in order to remove absorbed non-acid components, such as lower hydrocarbons, which after compression can be recycled to the second, or, if desired, the first step) and is then recycled to the absorption column of the second step. The gas mixture obtained in this regeneration can be discharged to the atmosphere after combustion if the quantity of sulphur compounds, in particular $H_2S$, still present therein, is low enough to fulfill the air pollution requirements. If the quantity of $H_2S$ present therein is too high, the gas becoming available from the regeneration column of the second mixture can be very suitably treated in a third absorption column at lower (in particular atmospheric) pressure with a (preferably liquid) absorbent in order to remove therefrom the $H_2S$ to such a degree that the gas becoming available from said absorption column can indeed be discharged to the atmosphere after combustion. In the latter case it is very suitable to use as absorbent part of the regenerated first mixture, and not to regenerate directly the resultant first mixture loaded with a small quantity of $H_2S$, but to supply it to the first step as part of the absorbent which is used in the first step. If desired, it is also possible to treat reduced offgas of a Claus process in said third absorption column to remove $H_2S$ from said gas.

The treatment of the gases in the first and second step is, if possible, carried out at the pressure at which the gas to be purified becomes available; pressures from atmospheric pressure to 120, in particular 10–100 $kg/cm^2$, are very suitable. The temperatures to be applied during said treatments may vary widely; temperatures of 15–90, in particular 15°–70° C., are very suitable.

The gas, purified from sulphur compounds and $CO_2$, which becomes available after the treatment in the second step, generally still contains water and lower hydrocarbons. These compounds can be removed in any suitable manner; the lower hydrocarbons, which mainly consist of hydrocarbons with 3–5 carbon atoms, are suitable condensed by cooling and removed. The purified gas finally obtained fulfills the requirements made in respect of its condensation and/or transport in the gaseous state.

The invention will be further illustrated with reference to the diagrammatic FIGS. 1 and 2.

Figure 1:
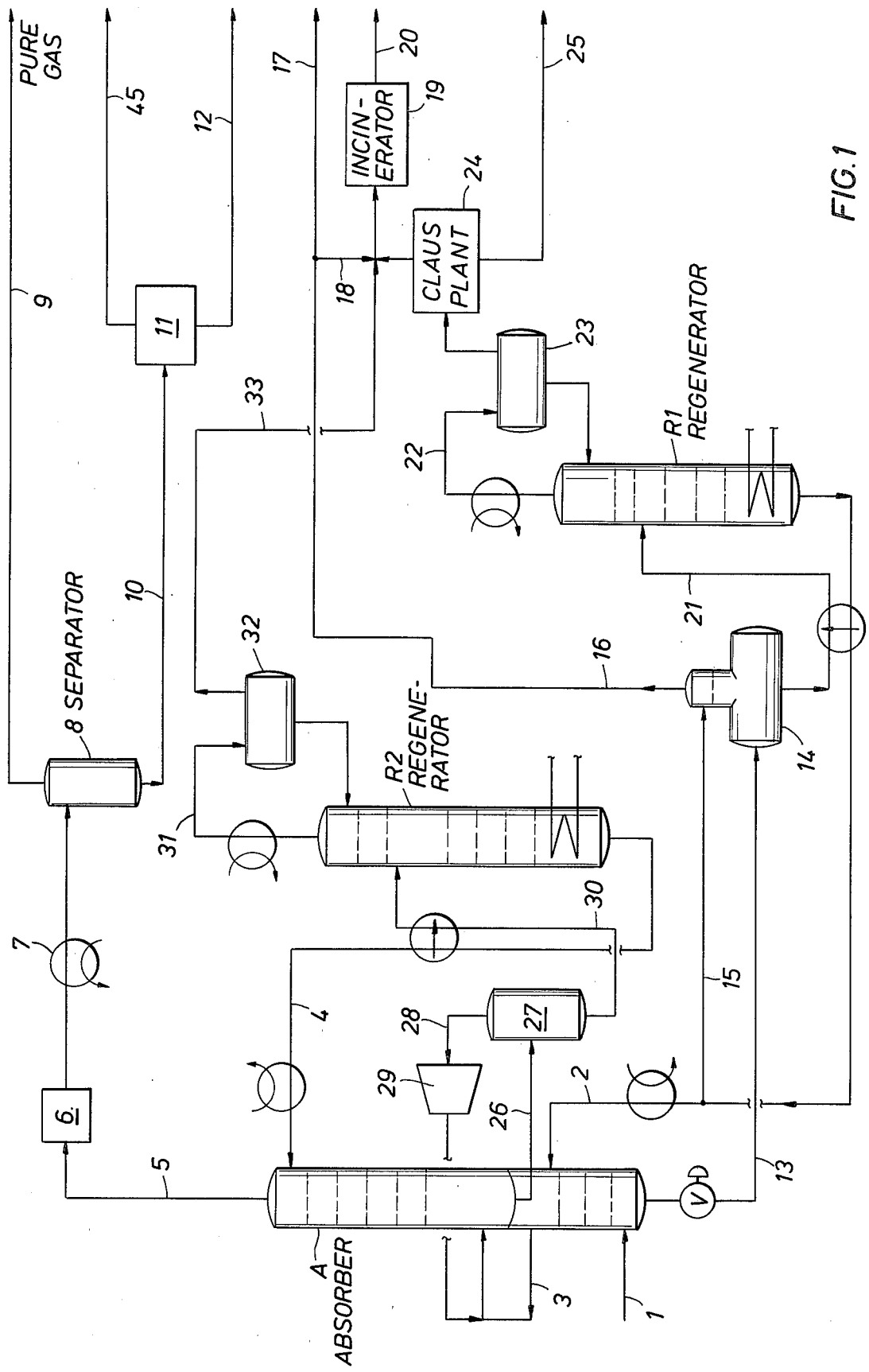
FIG. 1 illustrates an embodiment in which the gas to be purified contains substantially more $CO_2$ than $H_2S$.

More particularly, in FIG. 1 the gas to be purified is supplied through a line 1 to the bottom end of the lower part of a high-pressure absorption column A. In the lower part the column, the first step according to the invention is carried out by contacting the gas to be purified counter-currently in a short column with a mixture of a tertiary alkanol amine, sulfolane and water (first mixture), which is supplied through a line 2. The gas treated is discharged through a line 3 and supplied to the bottom end of the upper part of the high-pressure absorption column A. In the upper part the second step of the invention is carried out by contacting the gas supplied through the line 3 countercurrently with a mixture of a secondary or primary alkanol amine, sulfolane and water (second mixture), which is supplied through a line 4. The purified gas leaves A through a line 5, is freed from water in unit 6, cooled in cooler 7, and separated in separator 8 into pure gas (discharged through a line 9) and a mixture of light hydrocarbons discharged through a line 10. The mixture of light hydrocarbons is separated in unit 11 into liquid components (discharged through a line 12) and liberated gas (discharged through 45). The first mixture, loaded with acid gases, is discharged through a line 13 to vessel 14 where it expands, and liberated gas (mainly $CO_2$) is washed with a quantity of regenerated first mixture (supplied through a line 15). The resultant $CO_2$ is discharged through 16 and/or discharged to the atmosphere through 17, or, if necessary, supplied through 18 to incinerator 19 where any $H_2S$ present therein is incinerated, and the gas is subsequently discharged to the atmosphere through 20. The acid gas loaded first mixture obtained in vessel 14 is supplied through 21 to a regeneration column R1, where it is steam-stripped by indirect heating. The liberated gases, which have a high $H_2S$ content, are supplied through a line 22 and reflux vessel 23 to the Claus plant 24, where the $H_2S$ is converted into sulphur (discharged through 25); the liberated gases are combusted in incinerator 19 and discharged to the atmosphere through 20. The acid gas-loaded second mixture is discharged through 26 and expanded to atmospheric pressure in vessel 27. The liberated light hydrocarbons are discharged through 28, compressed in 29 and subsequently recycled to the bottom end of the upper part of column A through the line 3. The acid gas-loaded second mixture obtained in the vessel 27 is supplied to regeneration column R2 through a line 30 and steam-stripped by indirect heating. The regenerated second mixture is returned to A through the line 4. The gas mixture obtained from R2 is supplied to the incinerator 19 through 31, reflux vessel 32 and line 33.

Figure 2:
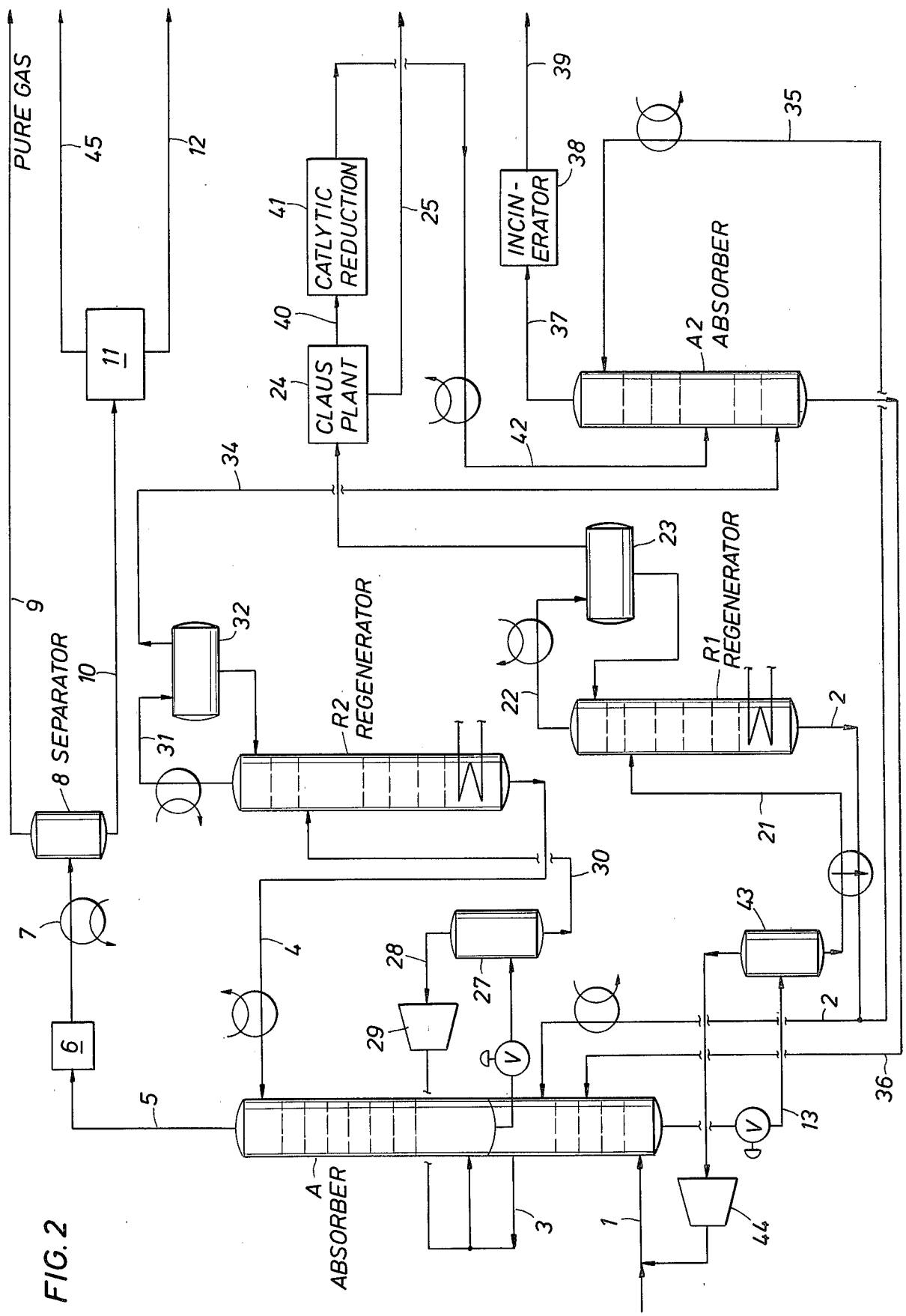
FIG. 2 represents the case where the quantities of $H_2S$ and $CO_2$ in the gas to be treated are approximately the same.

In the embodiment of FIG. 2 (where the same numerals refer to the same components as in FIG. 1) since the gas to be treated contains approximately equal quantities of $H_2S$ and $CO_2$, a somewhat different treatment of the acid gas-loaded absorbents obtained is more attractive. Since the gas liberated from the regeneration column R2 of the second mixture contains such a quantity of $H_2S$ that discharge to the atmosphere after combustion is undesirable, this gas is supplied through a line 34 to a selective absorption column A2 operating at atmospheric pressure, in which it is treated counter-currently with the regenerated first mixture (supplied through 35). The acid gas-loaded first mixture coming from the absorption column A2 is supplied through line 36 to the lower part of the high pressure absorption column A and further loaded therein by treatment with the starting gas supplied through 1. The gas leaving the absorption column A2 through 37 contains such a small quantity of $H_2S$ that after combustion in incinerator 38 it can be discharged to the atmosphere through a line 39. The gas becoming available from the Claus process through 40 also contains too large a quantity of sulphur compounds to be discharged to the atmosphere after combustion. Therefore, it is catalytically reduced in reactor 41 and the resultant $H_2S$-containing gas is introduced into the low-pressure absorption column A2 through a line 42.

The scheme represented in FIG. 2 also differs from that shown in FIG. 1 in that the loaded first mixture A leaving the lower part of the high-pressure absorption column A via line 13 is expanded in 43 before it is supplied to the regeneration column R1 through 21. The light hydrocarbons liberated during expansion are compressed in 44 and recycled with the starting gas.

What is claimed is:

1. A process for the treatment of a gas stream containing methane, light hydrocarbons, $H_2S$, and $CO_2$ comprising
    (a) contacting said gas stream at superatmospheric pressure in a first absorption zone with a first absorbent mixture which is selective for $H_2S$, said first absorbent mixture comprising from 5 percent to 35 percent by weight of water, from 15 to 50 percent by weight of physical absorbent, and from 10 to 60 percent by weight of chemical absorbent, said chemical absorbent comprising one or more tertiary amines, under conditions effective to absorb $H_2S$, and absorbing $H_2S$ and producing a gaseous stream containing methane, light hydrocarbons and $CO_2$, and a loaded absorbent solution;
    (b) passing the loaded absorbent solution to a first regeneration zone, regenerating the loaded absorbent solution and producing $H_2S$ and first absorbent mixture, and returning regenerated first absorbent mixture to the first absorption zone;
    (c) contacting the gaseous stream from the first absorption zone in a second absorption zone at superatmospheric pressure with a second absorbent mixture which is selective for $CO_2$ and $H_2S$, said second absorbent mixture comprising from 5 to 35 percent by weight of water, from 15 to 50 percent by weight of physical absorbent, and from 10 to 60 percent by weight of chemical absorbent, said chemical absorbent comprising one or more primary or secondary amines, under conditions effective to absorb $CO_2$ and any $H_2S$ remaining in the gaseous stream, and absorbing $CO_2$ and $H_2S$ remaining in the gaseous stream and obtaining a sweet gas stream containing methane and light hydrocarbons, and a loaded second absorbent solution;
    (d) passing the loaded second absorbent solution to a second regeneration zone, regenerating the loaded second absorbent solution and producing a $CO_2$ stream and second absorbent mixture, and returning regenerated second absorbent mixture to the second absorption zone; and
    (e) separating water and light hydrocarbons from the sweet gas stream.

2. The process of claim 1 wherein, in the first or second absorbent mixture, the physical absorbent is selected from N-methyl pyrrolidone, dimethyl formamide, dimethyl ether of polyethylene glycol, and sulfolane.

3. The process of claim 1 wherein, in the first absorbent mixture, the physical absorbent is sulfolane, and in the second absorbent mixture, the physical absorbent is sulfolane.

4. The process of claim 3 wherein the chemical absorbent of the first absorbent mixture comprises methyl diethanol amine and the chemical absorbent of the second absorbent mixture comprises di-isopropanol amine.

5. A process for the treatment of a gas stream containing methane, light hydrocarbons, $H_2S$, and $CO_2$ comprising
    (a) contacting said gas stream at superatmospheric pressure in a first absorption zone with a first absorbent mixture which is selective for $H_2S$, said first absorbent mixture comprising from 5 percent to 35 percent by weight of water, from 15 to 50 percent by weight of physical absorbent, and from 10 to 60 percent by weight of chemical absorbent, said chemical absorbent comprising one or more tertiary amines, under conditions effective to absorb $H_2S$, and absorbing $H_2S$ and producing a gaseous stream containing methane, light hydrocarbons and $CO_2$, and a loaded absorbent solution;
    (b) passing the loaded absorbent solution to a first regeneration zone, regenerating the loaded absorbent solution and producing $H_2S$ and first absorbent mixture, and returning regenerated first absorbent mixture to the first absorption zone;
    (c) contacting the gaseous stream from the first absorption zone in a second absorption zone at superatmospheric pressure with a second absorbent mixture which is selective for $CO_2$ and $H_2S$, said second absorbent mixture comprising from 5 to 35 percent by weight of water, from 15 to 50 percent by weight of physical absorbent, and from 10 to 60 percent by weight of chemical absorbent, said chemical absorbent comprising one or more primary or secondary amines, under conditions effective to absorb $CO_2$ and any $H_2S$ remaining in the gaseous stream, and absorbing $CO_2$ and $H_2S$ remaining in the gaseous stream and obtaining a sweet gas stream containing methane and light hydrocarbons, and a loaded second absorbent solution;

(d) passing the loaded second absorbent solution to a second regeneration zone, regenerating the loaded second absorbent solution and producing a $CO_2$ stream and second absorbent mixture, and returning regenerated second absorbent mixture to the second absorption zone;

(e) separating water and light hydrocarbons from the sweet gas stream;

(f) converting $H_2S$ from step (b) to sulphur and an effluent containing $SO_2$ in a Claus plant, and catalytically reducing $SO_2$ in said $SO_2$-containing effluent to produce an $H_2S$-containing stream;

(g) contacting the $CO_2$ stream from step (d) and the $H_2S$-containing stream from step (f) in a third absorption zone with an absorbent mixture which is selective for $H_2S$ under conditions effective to absorb $H_2S$ and removing the bulk of the $H_2S$ from said streams.

6. The process of claim 5 wherein, in the first or second absorbent mixture, the physical absorbent is selected from N-methyl pyrrolidone, dimethyl formamide, dimethyl ether of polyethylene glycol, and sulfolane.

7. The process of claim 5 wherein, in the first absorbent mixture, the physical absorbent is sulfolane, and in the second absorbent mixture, the physical absorbent is sulfolane.

8. The process of claim 7 wherein the chemical absorbent of the first absorbent mixture comprises methyl diethanol amine and the chemical absorbent of the second absorbent mixture comprises di-isopropanol amine.

9. The process of claim 5 wherein absorbent mixture, after absorbing $H_2S$ in the third absorption zone, is utilized in the first absorption zone as first absorbent mixture.

10. A process for the treatment of a gas stream containing methane, light hydrocarbons, $H_2S$, and $CO_2$ comprising (a) contacting said gas stream at superatmospheric pressure in a first absorption zone with a first absorbent mixture which is selective for $H_2S$, said first absorbent mixture comprising from 5 percent to 35 percent by weight of water, from 15 to 50 percent by weight of physical absorbent, and from 10 to 60 percent by weight of chemical absorbent, said chemical absorbent being selected from triethanol amine, diethyl ethanol amine, and methyl diethanol amine, under conditions effective to absorb $H_2S$, and absorbing $H_2S$ and producing a gaseous stream containing methane, light hydrocarbons and $CO_2$, and a loaded absorbent solution;

(b) passing the loaded absorbent solution to a first regeneration zone, regenerating the loaded absorbent solution and producing $H_2S$ and first absorbent mixture, and returning regenerated first absorbent mixture to the first absorption zone;

(c) contacting the gaseous stream from the first absorption zone in a second absorption zone at superatmospheric pressure with a second absorbent mixture which is selective for $CO_2$ and $H_2S$, said second absorbent mixture comprising from 5 to 35 percent by weight of water, from 15 to 50 percent by weight of physical absorbent, and from 10 to 60 percent by weight of chemical absorbent, said chemical absorbent being selected from ethanol amine, diethanol amine, and di-isopropanol amine, under conditions effective to absorb $CO_2$ and any $H_2S$ remaining in the gaseous stream, and absorbing $CO_2$ and $H_2S$ remaining in the gaseous stream and obtaining a sweet gas stream containing methane and light hydrocarbons, and a loaded second absorbent solution;

(d) passing the loaded second absorbent solution to a second regeneration zone, regenerating the loaded second absorbent solution and producing a $CO_2$ stream and second absorbent mixture, and returning regenerated second absorbent mixture to the second absorption zone; and (e) separating water and light hydrocarbons from the sweet gas stream.

11. The process of claim 10 wherein, in the first absorbent mixture, the physical absorbent is sulfolane, and in the second absorbent mixture, the physical absorbent is sulfolane.

12. A process for the treatment of a gas stream containing methane, light hydrocarbons, $H_2S$, and $CO_2$ comprising (a) contacting said gas stream at superatmospheric pressure in a first absorption zone with a first absorbent mixture which is selective for $H_2S$, said first absorbent mixture comprising from 5 percent to 35 percent by weight of water, from 15 to 50 percent by weight of physical absorbent, and from 10 to 60 percent by weight of chemical absorbent, said chemical absorbent being selected from triethanol amine, diethyl ethanol amine, and methyl diethanol amine, under conditions effective to absorb $H_2S$, and absorbing $H_2S$ and producing a gaseous stream containing methane, light hydrocarbons and $CO_2$, and a loaded absorbent solution;

(b) passing the loaded absorbent solution to a first regeneration zone, regenerating the loaded absorbent solution and producing $H_2S$ and first absorbent mixture, and returning regenerated first absorbent mixture to the first absorption zone;

(c) contacting the gaseous stream from the first absorption zone in a second absorption zone at superatmospheric pressure with a second absorbent mixture which is selective for $CO_2$ and $H_2S$, said second absorbent mixture comprising from 5 to 35 percent by weight of water, from 15 to 50 percent by weight of physical absorbent, and from 10 to 60 percent by weight of chemical absorbent, said chemical absorbent being selected from ethanol amine, diethanol amine, and di-isopropanol amine, under conditions effective to absorb $CO_2$ and any $H_2S$ remaining in the gaseous stream, and absorbing $CO_2$ and $H_2S$ remaining in the gaseous stream and obtaining a sweet gas stream containing methane and light hydrocarbons, and a loaded second absorbent solution;

(d) passing the loaded second absorbent solution to a second regeneration zone, regenerating the loaded second absorbent solution and producing a $CO_2$ stream and second absorbent mixture, and returning regenerated second absorbent mixture to the second absorption zone;

(e) separating water and light hydrocarbons from the sweet gas stream;

(f) converting H₂S from step (b) to sulphur and an effluent containing SO₂ in a Claus plant, and catalytically reducing SO₂ in said SO₂-containing effluent to produce an H₂S-containing stream;

(g) contacting the CO₂ stream from step (d) and the H₂S-containing stream from step (f) in a third absorption zone with an absorbent mixture which is selective for H₂S under conditions effective to absorb H₂S and removing the bulk of the H₂S from said streams.

13. The process of claim 12 wherein, in the first absorbent mixture, the physical absorbent is sulfolane, and in the second absorbent mixture, the physical absorbent is sulfolane.

* * * * *